(12) United States Patent
Xie et al.

(10) Patent No.: US 9,981,853 B2
(45) Date of Patent: May 29, 2018

(54) MOLECULAR SIEVE SSZ-107, ITS SYNTHESIS AND USE

(71) Applicant: Chevron U.S.A. Inc., San Ramon, CA (US)

(72) Inventors: Dan Xie, Richmond, CA (US); Cong-Yan Chen, Kensington, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 0 days. days.

(21) Appl. No.: 15/643,553

(22) Filed: Jul. 7, 2017

(65) Prior Publication Data

US 2018/0093896 A1    Apr. 5, 2018

Related U.S. Application Data

(60) Provisional application No. 62/404,256, filed on Oct. 5, 2016.

(51) Int. Cl.
| | |
|---|---|
| *C01B 39/48* | (2006.01) |
| *B01J 29/70* | (2006.01) |
| *C07C 1/20* | (2006.01) |
| *B01J 37/04* | (2006.01) |
| *B01J 37/10* | (2006.01) |
| *B01J 37/00* | (2006.01) |
| *B01J 37/06* | (2006.01) |
| *B01D 53/86* | (2006.01) |
| *B01D 53/94* | (2006.01) |

(52) U.S. Cl.
CPC .......... *C01B 39/48* (2013.01); *B01D 53/8628* (2013.01); *B01D 53/9418* (2013.01); *B01J 29/70* (2013.01); *B01J 37/009* (2013.01); *B01J 37/04* (2013.01); *B01J 37/06* (2013.01); *B01J 37/10* (2013.01); *C07C 1/20* (2013.01); *B01D 2255/2092* (2013.01); *B01D 2255/30* (2013.01); *C01P 2002/72* (2013.01); *C01P 2002/74* (2013.01); *C01P 2004/03* (2013.01); *C07C 2529/70* (2013.01); *C07C 2529/72* (2013.01); *C07C 2529/74* (2013.01); *C07C 2529/76* (2013.01); *C07C 2529/78* (2013.01)

(58) Field of Classification Search
CPC ....... C01B 39/48; B01J 29/70; B01D 53/9418
See application file for complete search history.

(56) References Cited

U.S. PATENT DOCUMENTS

| | | | |
|---|---|---|---|
| 9,108,856 B2 * | 8/2015 | Elomari | ................. C01B 39/48 |
| 9,192,924 B1 * | 11/2015 | Zones | ..................... B01J 20/18 |
| 9,550,684 B2 | 1/2017 | Weston et al. | |

(Continued)

FOREIGN PATENT DOCUMENTS

| | | |
|---|---|---|
| CN | 104418343 | 3/2015 |
| EP | 1701913 B1 | 9/2006 |
| WO | 2014200633 A1 | 12/2014 |

OTHER PUBLICATIONS

PCT International Search Report, International Appl. No. PCT/US2017/041073, dated Oct. 6, 2017.

*Primary Examiner* — David M Brunsman
(74) *Attorney, Agent, or Firm* — Terrence M. Flaherty (57) ABSTRACT

This disclosure is directed to a novel crystalline molecular sieve designated as SSZ-107, its synthesis using 1,1-diethylpyrrolidinium cations as a structure directing agent, and its use as an adsorbent and/or a catalyst.

15 Claims, 3 Drawing Sheets

(56) References Cited

U.S. PATENT DOCUMENTS

2015/0266007 A1* 9/2015 Mancka ............ B01D 53/9418
 502/60
2016/0068400 A1* 3/2016 Davis ..................... C01B 39/46
 423/718

* cited by examiner

MOLECULAR SIEVE SSZ-107, ITS SYNTHESIS AND USE

CROSS-REFERENCE TO RELATED APPLICATIONS

This application claims priority to U.S. Provisional Patent Application Ser. No. 62/404,256 filed on Oct. 5, 2016, herein incorporated by reference in its entirety.

TECHNICAL FIELD

This disclosure relates to a novel molecular sieve material designated as SSZ-107, its synthesis, and its use as an adsorbent and a catalyst.

BACKGROUND

Molecular sieve materials, both natural and synthetic, have been demonstrated in the past to be useful as adsorbents and to have catalytic properties for various types of organic conversion reactions. Certain molecular sieves, such as zeolites, aluminophosphates, and mesoporous materials, are ordered, porous crystalline materials having a definite crystalline structure as determined by X-ray diffraction. Within the crystalline molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Although many different crystalline molecular sieves have been discovered, there is a continuing need for new molecular sieves with desirable properties for gas separation and drying, organic conversion reactions, and other applications. New molecular sieves can contain novel internal pore architectures, providing enhanced selectivities in these processes.

SUMMARY

The present disclosure is directed to a novel family of crystalline molecular sieves with unique properties, referred to herein as "molecular sieve SSZ-107" or simply "SSZ-107."

In one aspect, there is provided a molecular sieve having, in its as-synthesized form, and X-ray diffraction pattern including the peaks listed in Table 2.

In its as-synthesized and anhydrous form, molecular sieve SSZ-107 has a chemical composition comprising the following molar relationship:

|  | Broad | Exemplary |
| --- | --- | --- |
| $SiO_2/Al_2O_3$ | 5 to 25 | 5 to 15 |
| $Q/SiO_2$ | >0 to 0.1 | >0 to 0.1 |
| $M/SiO_2$ | >0 to 0.1 | >0 to 0.1 | wherein compositional variables Q comprises 1,1-diethylpyrrolidinium cations and M is a Group 1 or Group 2 metal.

In another aspect, there is provided a molecular sieve having, in its calcined form, an X-ray diffraction pattern including the peaks listed in Table 3.

In its calcined form, molecular sieve SSZ-107 has a chemical composition, in terms of mole ratios, comprising the following:

wherein n has a value of from 5 to 25.

In a further aspect, there is provided a method of synthesizing molecular sieve SSZ-107, the method comprising (a) preparing a reaction mixture comprising: (1) a source of silicon oxide; (2) a source of aluminum oxide; (3) a source of a Group 1 or Group 2 metal; (4) a structure directing agent comprising 1,1-diethylpyrrolidinium cations; (5) hydroxide ions; and (6) water; and (b) subjecting the reaction mixture to crystallization conditions sufficient to form crystals of the molecular sieve.

In yet a further aspect, there is provided an organic compound conversion process comprising contacting an organic compound under organic compound conversion conditions with a catalyst comprising the molecular sieve described herein.

In still yet a further aspect, there is provided a process of selectively reducing nitrogen oxides ($NO_x$), comprising contacting a gaseous stream containing nitrogen oxides, with a catalyst comprising the molecular sieve described herein.

DETAILED DESCRIPTION

In general, molecular sieve SSZ-107 is prepared by: (a) preparing a reaction mixture containing (1) a source of silicon oxide; (2) a source of aluminum oxide; (3) a source of a Group 1 or Group 2 metal (M); (4) a structure directing agent (Q) comprising 1,1-diethylpyrrolidinium cations; (5) hydroxide ions; and (6) water; and (b) subjecting the reaction mixture to crystallization conditions sufficient to form crystals of the molecular sieve.

The composition of the reaction mixture from which the molecular sieve is formed, in terms of mole ratios, is identified in Table 1 below:

TABLE 1

| Reactants | Broad | Exemplary |
| --- | --- | --- |
| $SiO_2/Al_2O_3$ | 5 to 100 | 15 to 80 |
| $M/SiO_2$ | 0.05 to 1.00 | 0.10 to 0.50 |
| $Q/SiO_2$ | 0.05 to 0.50 | 0.10 to 0.35 |
| $OH/SiO_2$ | 0.10 to 1.00 | 0.20 to 0.60 |
| $H_2O/SiO_2$ | 10 to 100 | 10 to 40 | wherein compositional variables Q and M are as described herein above.

Suitable sources of silicon oxide include colloidal silica, fumed silica, precipitated silica, alkali metal silicates, and tetraalkyl orthosilicates.

Suitable sources of aluminum oxide include hydrated alumina and water-soluble aluminum salts (e.g., aluminum nitrate).

Combined sources of silicon oxide and aluminum oxide can additionally or alternatively be used and can include aluminosilicate zeolites (e.g., zeolite Y) and clays or treated clays (e.g., metakaolin).

The structure directing agent (Q) comprises 1,1-diethylpyrrolidinium cations, represented by the following structure (1):

(1)

Suitable sources of Q are the hydroxides, chlorides, bromides, and/or other salts of the quaternary ammonium compound.

The reaction mixture may contain seeds of a molecular sieve material, such as SSZ-107 crystals from a previous synthesis, in an amount of from 0.01 to 10,000 ppm by weight (e.g., 100 to 5000 ppm by weight) of the reaction mixture.

For each embodiment described herein, the molecular sieve reaction mixture can be supplied by more than one source. Also, two or more reaction components can be provided by one source.

The reaction mixture can be prepared either batch wise or continuously. Crystal size, morphology and crystallization time of the molecular sieve described herein can vary with the nature of the reaction mixture and the crystallization conditions.

Crystallization and Post-Synthesis Treatment

Crystallization of the molecular sieve from the above reaction mixture can be carried out under either static, tumbled or stirred conditions in a suitable reactor vessel, such as for example polypropylene jars or Teflon-lined or stainless steel autoclaves, at a temperature of from 100° C. to 200° C. (e.g., 120° C. to 160° C.) for a time sufficient for crystallization to occur at the temperature used, e.g., from 1 day to 10 days. Crystallization is usually carried out in a closed system under autogenous pressure.

Once the molecular sieve crystals have formed, the solid product is recovered from the reaction mixture by standard mechanical separation techniques such as centrifugation or filtration. The crystals are water-washed and then dried to obtain the as-synthesized molecular sieve crystals. The drying step is typically performed at a temperature of less than 200° C.

As a result of the crystallization process, the recovered crystalline molecular sieve product contains within its pore structure at least a portion of the structure directing agent used in the synthesis.

The molecular sieve described herein may be subjected to subsequent treatment to remove part or all of the organic structure directing agent used in its synthesis. This can be conveniently effected by thermal treatment in which the as-synthesized material can be heated at a temperature of at least 370° C. for at least 1 minute and not longer than 24 hours. While sub-atmospheric and/or super-atmospheric pressures can be employed for the thermal treatment, atmospheric pressure may typically be desired for reasons of convenience. The thermal treatment can be performed at a temperature up to 925° C. Additionally or alternatively, the organic structure directing agent can be removed by treatment with ozone (see, e.g., A. N. Parikh et al., *Micropor. Mesopor. Mater.* 2004, 76, 17-22).

To the extent desired, the original Group 1 or Group 2 metal cations in the molecular sieve can be replaced in accordance with techniques well known in the art by ion exchange with other cations. Preferred replacing cations include metal ions, hydrogen ions, hydrogen precursor, e.g., ammonium ions and mixtures thereof. Particularly preferred replacing cations are those which tailor the catalytic activity for certain organic conversion reactions. These include hydrogen, rare earth metals and metals of Groups 2 to 15 of the Periodic Table of the Elements.

The present molecular sieve can be formulated into a catalyst composition by combination with other materials, such as binders and/or matrix materials, which provide additional hardness or catalytic activity to the finished catalyst.

Materials which can be blended with the present molecular sieve can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of SSZ-107 contained in the final catalyst product can range from 1 to 90 wt. % (e.g., 2 to 80 wt. %) of the total catalyst.

Characterization of the Molecular Sieve

In its as-synthesized and anhydrous form, molecular sieve SSZ-107 has a chemical composition comprising the following molar relationship:

|  | Broad | Exemplary |
|---|---|---|
| $SiO_2/Al_2O_3$ | 5 to 25 | 5 to 15 |
| $Q/SiO_2$ | >0 to 0.1 | >0 to 0.1 |
| $M/SiO_2$ | >0 to 0.1 | >0 to 0.1 | wherein compositional variables Q and M are as described herein above.

It should be noted that the as-synthesized form of the molecular sieve disclosed herein may have molar ratios different from the molar ratios of reactants of the reaction mixture used to prepare the as-synthesized form. This result may occur due to incomplete incorporation of 100% of the reactants of the reaction mixture into the crystals formed (from the reaction mixture).

In its calcined form, molecular sieve SSZ-107 has a chemical composition comprising the following molar relationship:

$$Al_2O_3:(n)SiO_2$$

wherein n has a value of from 5 to 25 (e.g., 5 to 20, or 5 to 15).

The novel molecular sieve structure SSZ-107 is characterized by an X-ray diffraction pattern, which in the as-synthesized form of the molecular sieve, includes at least the lines listed in Table 2 below and which, in the calcined form of the molecular sieve, includes at least the peaks listed in Table 3 below.

TABLE 2

Characteristic Peaks for As-Synthesized SSZ-107

| 2-Theta[a] | d-Spacing, nm | Relative Intensity[b] | Peak Broadening[c] |
|---|---|---|---|
| 7.58 | 1.166 | W | B |
| 9.59 | 0.922 | M | B |
| 12.93 | 0.684 | M | Sh |
| 14.09 | 0.628 | W | B |
| 16.16 | 0.548 | W | B |
| 17.78 | 0.498 | M | Sh |
| 20.03 | 0.443 | W | B |
| 20.74 | 0.428 | VS | B |
| 22.04 | 0.403 | W | Sh |
| 22.51 | 0.395 | W | Sh |
| 23.26 | 0.382 | W | B |
| 25.18 | 0.353 | W | B |
| 26.05 | 0.342 | M | Sh |
| 27.89 | 0.320 | W | B |
| 30.30 | 0.295 | M | B |
| 30.82 | 0.290 | S | B |
| 31.47 | 0.284 | W | B |

[a] ±0.20
[b] The powder XRD patterns provided are based on a relative intensity scale in which the strongest line in the X-ray diffraction pattern is assigned a value of 100: W = weak (>0 to ≤20); M = medium (>20 to ≤40); S = strong (>40 to ≤60); VS = very strong (>60 to ≤100).
[c] Peak Broadening is characterized by the Full-Width at Half Maximum (FWHM) of the XRD peak. Based on the FWHM values, the peaks are classified as: Sh = sharp (≤2*smallest FWHM); B = broad (>2*smallest FWHM).

TABLE 3

Characteristic Peaks for Calcined SSZ-107

| 2-Theta[a] | d-Spacing, nm | Relative Intensity[b] | Peak Broadening[c] |
|---|---|---|---|
| 7.54 | 1.172 | W | B |
| 9.50 | 0.930 | M | B |
| 12.94 | 0.684 | S | Sh |
| 14.09 | 0.628 | W | B |
| 16.16 | 0.548 | W | B |
| 17.84 | 0.498 | M | Sh |
| 20.03 | 0.443 | W | B |
| 20.74 | 0.428 | VS | B |
| 22.91 | 0.388 | W | Sh |
| 24.70 | 0.360 | W | B |
| 26.03 | 0.342 | M | Sh |
| 27.98 | 0.319 | W | B |
| 30.34 | 0.294 | M | B |
| 30.74 | 0.291 | S | B |
| 31.78 | 0.281 | W | B |

[a] ±0.20
[b] The powder XRD patterns provided are based on a relative intensity scale in which the strongest line in the X-ray diffraction pattern is assigned a value of 100: W = weak (>0 to ≤20); M = medium (>20 to ≤40); S = strong (>40 to ≤60); VS = very strong (>60 to ≤100).
[c] Peak Broadening is characterized by the Full-Width at Half Maximum (FWHM) of the XRD peak. Based on the FWHM values, the peaks are classified as: Sh = sharp (≤2*smallest FWHM); B = broad (>2*smallest FWHM).

The powder X-ray diffraction patterns presented herein were collected by standard techniques. The radiation was CuK$_\alpha$ radiation. The peak heights and the positions, as a function of 2θ where θ is the Bragg angle, were read from the relative intensities of the peaks (adjusting for background), and d, the interplanar spacing corresponding to the recorded lines, can be calculated.

Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation. Calcination can also cause minor shifts in the XRD pattern. Notwithstanding these minor perturbations, the basic crystal lattice structure remains unchanged.

Processes Using SSZ-107

Molecular sieve SSZ-107 can be used to dry gases and liquids; for selective molecular separation based on size and polar properties; as an ion-exchanger; as a chemical carrier; in gas chromatography; and as a catalyst. Examples of suitable catalytic uses include organic compound conversion reactions, the synthesis of monoalkylamines and dialkylamines, the conversion of organic oxygenates to olefins, and the catalytic reduction of nitrogen oxides.

One suitable use of molecular sieve SSZ-107 is in the catalytic conversion of organic oxygenates to one or more olefins, particularly ethylene and propylene. The term "organic oxygenates" is defined herein to include aliphatic alcohols, ethers, carbonyl compounds (e.g., aldehydes, ketones, carboxylic acids, carbonates, and the like), and compounds containing hetero-atoms, such as, halides, mercaptans, sulfides, amines, and mixtures thereof. The aliphatic moiety normally contains from 1 to 10 carbon atoms (e.g., 1 to 4 carbon atoms).

Representative organic oxygenates include lower straight chain or branched aliphatic alcohols, their unsaturated counterparts, and their nitrogen, halogen, and sulfur analogs. Examples of suitable organic oxygenate compounds include methanol; ethanol; n-propanol; isopropanol; $C_4$ to $C_{10}$ alcohols; methyl ethyl ether; dimethyl ether; diethyl ether; diisopropyl ether; formaldehyde; dimethyl carbonate; acetone; acetic acid; n-alkyl amines, n-alkyl halides, n-alkyl sulfides having n-alkyl groups in a range of from 3 to 10 carbon atoms; and mixtures thereof. Particularly suitable oxygenate compounds are methanol, dimethyl ether, or combinations thereof, especially methanol.

In the present oxygenate conversion process, a feedstock comprising an organic oxygenate, optionally, with one or more diluents, is contacted in the vapor phase in a reaction zone with a catalyst comprising the molecular sieve of the present disclosure at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from 1 to 99 mol % of the total feed mixture.

The temperature employed in the oxygenate conversion process may vary over a wide range, such as from 200° C. to 1000° C. (e.g., 250° C. to 800° C., 300° C. to 650° C., or 400° C. to 600° C.).

Light olefin products will form, although not necessarily in optimum amounts, at a wide range of pressures, including autogenous pressures and pressures in the range of from 0.1 kPa to 10 MPa (e.g., 7 kPa to 5 MPa, or 50 kPa to 1 MPa). The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The oxygenate conversion process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor), and the selected process design characteristics.

A wide range of weight hourly space velocities (WHSV) can be used in the present oxygenate conversion process. WHSV is defined as weight of feed (excluding diluent) per hour per weight of a total reaction volume of molecular sieve catalyst (excluding inerts and/or fillers). The WHSV generally may be in the range of from 0.01 to 500 h$^{-1}$ (e.g., 0.5 to 300 h$^{-1}$, or 1 to 200 h$^{-1}$).

Another suitable use of molecular sieve SSZ-107 is in the selective catalytic reduction (SCR) of nitrogen oxides. In this process, a gaseous stream comprising nitrogen oxides (NO$_x$) is selectively reduced in the presence of a reductant and a catalyst comprising molecular sieve SSZ-107. The nitrogen oxides (principally NO and NO$_2$) are reduced to N$_2$ while the reductant is oxidized. When ammonia is the reductant, N$_2$ is also an oxidation product. Ideally, the only reaction products are water and N$_2$, although some NH$_3$ is usually oxidized with air to NO or N$_2$O.

To promote the catalytic activity, one more transition metals may be incorporated into the molecular sieve support. Any suitable transition metal may be selected. Transition metals particularly effective for use during selective catalytic reduction include one or more of Cr, Mn, Fe, Co, Ce, Ni, Cu, Mo, Ru, Rh, Pd, Ag, Re, Ir, and Pt. In one embodiment, the transition metal is selected from Fe and Cu. In an exemplary embodiment, the transition metal is Cu. Any suitable and effective amount of transition metal may be used in the catalyst. The total amount of the transition metal(s) that may be included in the molecular sieve may be from 0.01 to 20 wt. % (e.g., 0.1 to 10 wt. %, 0.5 to 5 wt. %, or 1 to 2.5 wt. %) based on the total weight of the molecular sieve support.

The molecular sieve catalyst may be used in any suitable form. For example, the molecular sieve catalyst may be used in powder form, as extrudates, as pellets, or in any other suitable form.

The molecular sieve catalyst for use in the reduction of nitrogen oxides may be coated on a suitable substrate monolith or can be formed as extruded-type catalysts, but is preferably used in a catalyst coating. In one embodiment, the molecular sieve catalyst is coated on a flow-through monolith substrate (i.e., a honeycomb monolithic catalyst support structure with many small, parallel channels running axially through the entire part) or filter monolith substrate, such as a wall-flow filter, etc. The molecular sieve catalyst for use herein may be coated (e.g., as a washcoat component) on a suitable monolith substrate, such as a metal or ceramic flow through monolith substrate or a filtering substrate, such as a wall-flow filter or sintered metal or partial filter. Alternatively, the molecular sieve may be synthesized directly onto the substrate and/or may be formed into an extruded-type flow through catalyst.

The gaseous stream comprising nitrogen oxides may contain one or more of NO, NO$_2$, and N$_2$O in addition to other non-NO$_x$ gases such as N$_2$, O$_2$, CO, CO$_2$, SO$_2$, HCl and H$_2$O. The exhaust gas may contain from 1 to 10,000 ppm (e.g., 10 to 1,000 ppm, or 50 to 500 ppm) of NO.

The reductant can be a nitrogen compound or a short-chain (C$_1$ to C$_8$) hydrocarbon. Preferably, the reductant is a nitrogen compound. Suitable nitrogen compounds include ammonia, hydrazine, and ammonia precursors (e.g., urea, ammonium carbonate, ammonium carbamate, ammonium hydrogen carbonate, and ammonium formate).

The gaseous stream comprising nitrogen oxides can contact the catalyst at a gas hourly space velocity of from 5000 to 500,000 h$^{-1}$ (e.g., 10,000 to 200,000 h$^{-1}$).

The reduction of nitrogen oxides may be carried out at a temperature within the range of 100° C. to 650° C. (e.g., 250° C. to 600° C.).

The reduction of nitrogen oxides may be carried out in the presence of oxygen or in the absence of oxygen.

EXAMPLES

The following illustrative examples are intended to be non-limiting.

Example 1

12.09 g of deionized water, 1.29 g of 50% NaOH solution, 5.85 g of 20% 1,1-diethylpyrrolidinium hydroxide (SACHEM, Inc.) and 2.00 g of CBV760 Y-zeolite powder (Zeolyst International, SiO$_2$/Al$_2$O$_3$ mole ratio=60) were mixed together in a Teflon liner. The resulting gel was stirred until it became homogeneous. The liner was then capped and placed within a Parr steel autoclave reactor. The autoclave was then placed in an oven and the heated at 135° C. for 5 days. The solid products were recovered by centrifugation, washed with deionized water and dried at 95° C.

Figure 1:
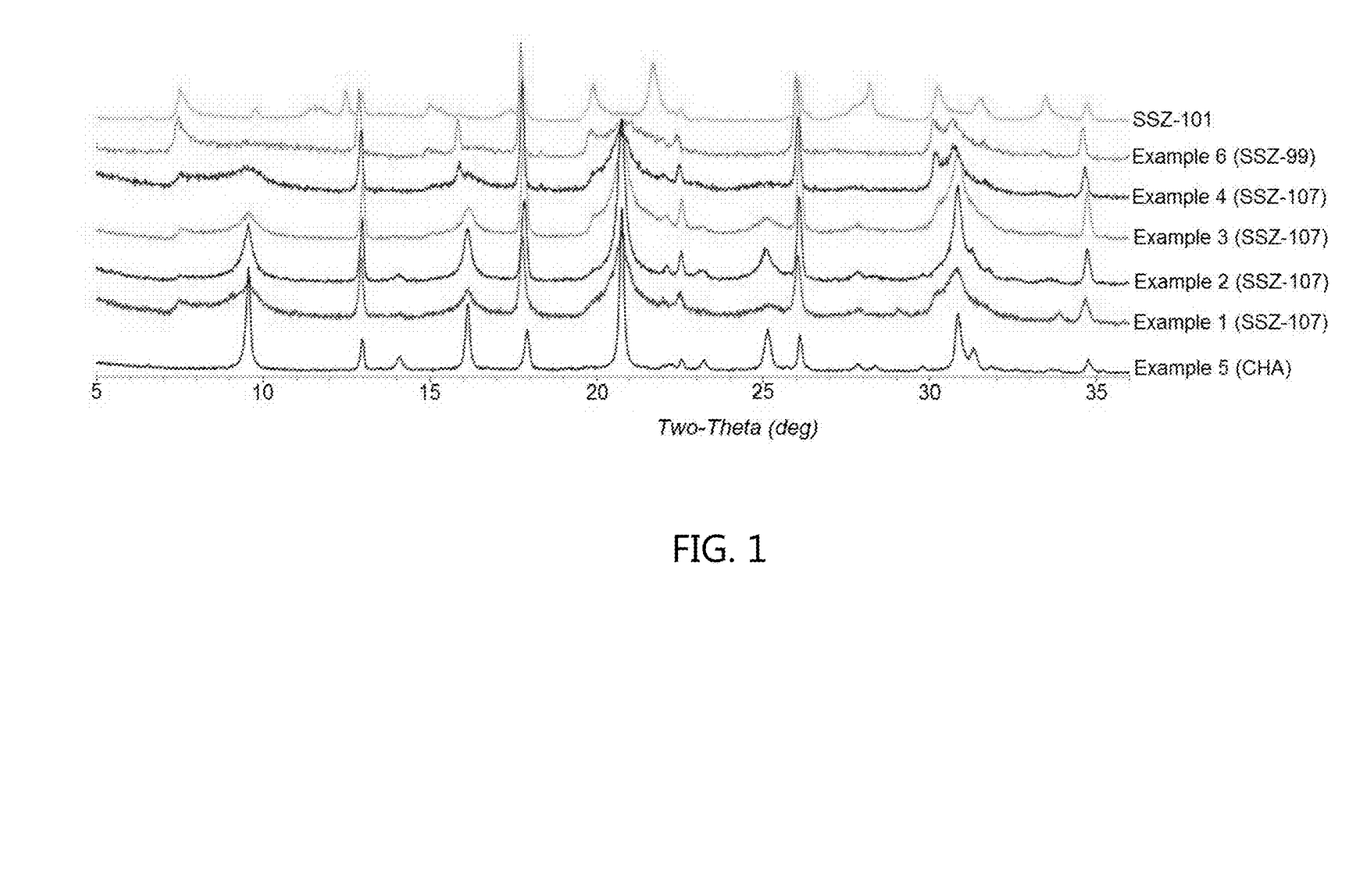
FIG. 1 shows the powder X-ray diffraction (XRD) patterns of the as-synthesized molecular sieves of Examples 1-6 and molecular sieve SSZ-101.
Figure 2:
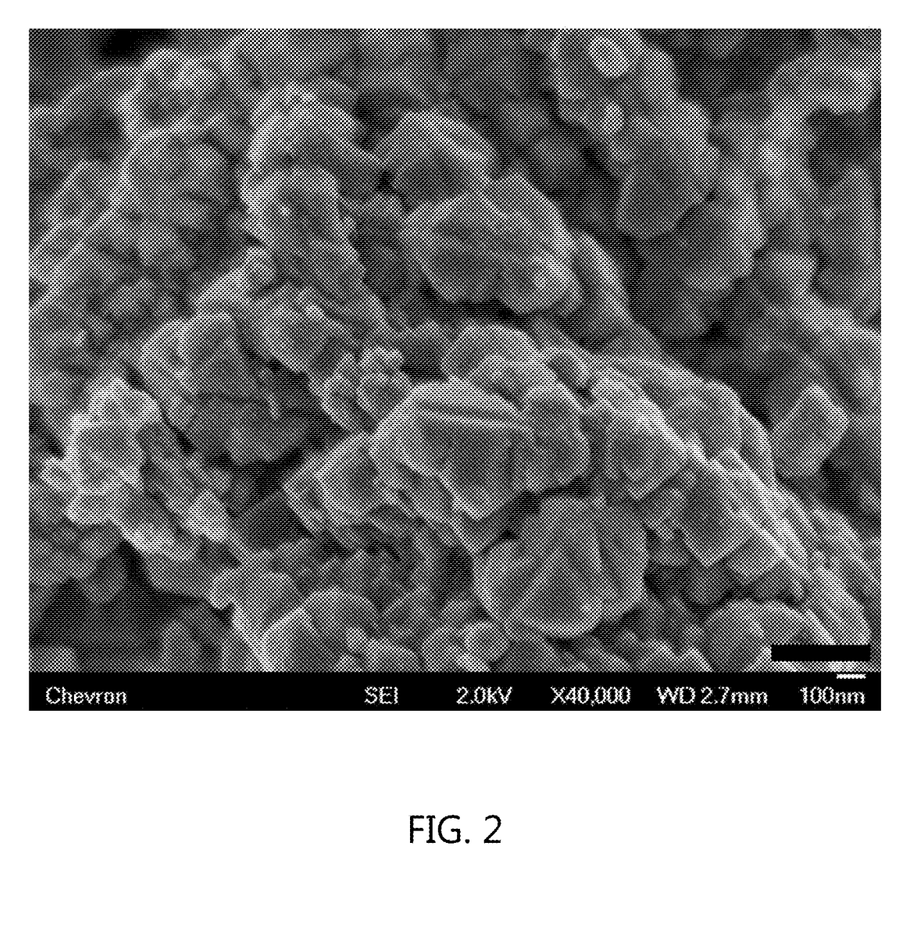
FIG. 2 is a Scanning Electron Micrograph (SEM) image of the as-synthesized molecular sieve of Example 1.

Powder XRD of the as-synthesized product gave the pattern indicated in FIG. 1 and showed the product to be a pure form of a new phase, SSZ-107. A SEM image of the as-synthesized product is shown in FIG. 2.

The as-synthesized product has a SiO$_2$/Al$_2$O$_3$ mole ratio of 9.43, as determined by ICP elemental analysis.

Example 2

5.19 g of deionized water, 1.29 g of 50% NaOH solution, 3.51 g of 20% 1,1-diethylpyrrolidinium hydroxide (SACHEM, Inc.) and 2.00 g of CBV760 Y-zeolite powder (Zeolyst International, SiO$_2$/Al$_2$O$_3$ mole ratio=60) were mixed together in a Teflon liner. The resulting gel was stirred until it became homogeneous. The liner was then capped and placed within a Parr steel autoclave reactor. The autoclave was then placed in an oven and the heated at 150° C. for 4 days. The solid products were recovered by centrifugation, washed with deionized water and dried at 95° C.

Powder XRD of the as-synthesized product gave the pattern indicated in FIG. 1 and showed the product to be pure SSZ-107.

The as-synthesized product has a SiO$_2$/Al$_2$O$_3$ mole ratio of 11.02, as determined by ICP elemental analysis.

Example 3

3.54 g of deionized water, 3.22 g of 50% NaOH solution, 11.70 g of 20% 1,1-diethylpyrrolidinium hydroxide (SACHEM, Inc.) and 5.00 g of CBV760 Y-zeolite powder (Zeolyst International, SiO$_2$/Al$_2$O$_3$ mole ratio=60) were mixed together in a Teflon liner. The resulting gel was stirred until it became homogeneous. The liner was then capped and placed within a Parr steel autoclave reactor. The autoclave was then placed in an oven and the heated at 135° C. for 5 days. The solid products were recovered by centrifugation, washed with deionized water and dried at 95° C.

Powder XRD of the as-synthesized product gave the pattern indicated in FIG. 1 and showed the product to be pure SSZ-107.

The as-synthesized product has a SiO$_2$/Al$_2$O$_3$ mole ratio of 9.17, as determined by ICP elemental analysis.

Example 4

27.88 g of deionized water, 3.22 g of 50% NaOH solution, 17.55 g of 20% 1,1-diethylpyrrolidinium hydroxide (SA-CHEM, Inc.) and 5.00 g of CBV760 Y-zeolite powder (Zeolyst International, SiO$_2$/Al$_2$O$_3$ mole ratio=60) were mixed together in a Teflon liner. The resulting gel was stirred until it became homogeneous. The liner was then capped and placed within a Parr steel autoclave reactor. The autoclave was then placed in an oven and the heated at 135° C. for 5 days. The solid products were recovered by centrifugation, washed with deionized water and dried at 95° C.

Powder XRD of the as-synthesized product gave the pattern indicated in FIG. 1 and showed the product to be pure SSZ-107.

The as-synthesized product has a SiO$_2$/Al$_2$O$_3$ mole ratio of 8.76, as determined by ICP elemental analysis.

Example 5

34.74 g of deionized water, 3.22 g of 50% NaOH solution, 8.77 g of 20% 1,1-diethylpyrrolidinium hydroxide (SA-CHEM, Inc.) and 5.00 g of CBV760 Y-zeolite powder (Zeolyst International, SiO$_2$/Al$_2$O$_3$ mole ratio=60) were mixed together in a Teflon liner. The resulting gel was stirred until it became homogeneous. The liner was then capped and placed within a Parr steel autoclave reactor. The autoclave was then placed in an oven and the heated at 135° C. for 4 days. The solid products were recovered by centrifugation, washed with deionized water and dried at 95° C.

Powder XRD of the as-synthesized product gave the pattern indicated in FIG. 1 and showed the product to be pure CHA-type zeolite.

Example 6

30.22 g of deionized water, 3.22 g of 50% NaOH solution, 14.62 g of 20% 1,1-diethylpyrrolidinium hydroxide (SA-CHEM, Inc.) and 5.00 g of CBV760 Y-zeolite powder (Zeolyst International, SiO$_2$/Al$_2$O$_3$ mole ratio=60) were mixed together in a Teflon liner. The resulting gel was stirred until it became homogeneous. The liner was then capped and placed within a Parr steel autoclave reactor. The autoclave was then placed in an oven and the heated at 135° C. for 5 days. The solid products were recovered by centrifugation, washed with deionized water and dried at 95° C.

Powder XRD of the as-synthesized product gave the pattern indicated in FIG. 1 and showed the product to be pure SSZ-99.

Example 7

The as-synthesized molecular sieve product of Example 1 was calcined inside a muffle furnace under a flow of air heated to 540° C. at a rate of 1° C./minute and held at 540° C. for 5 hours, cooled and then analyzed by powder XRD.

Figure 3:
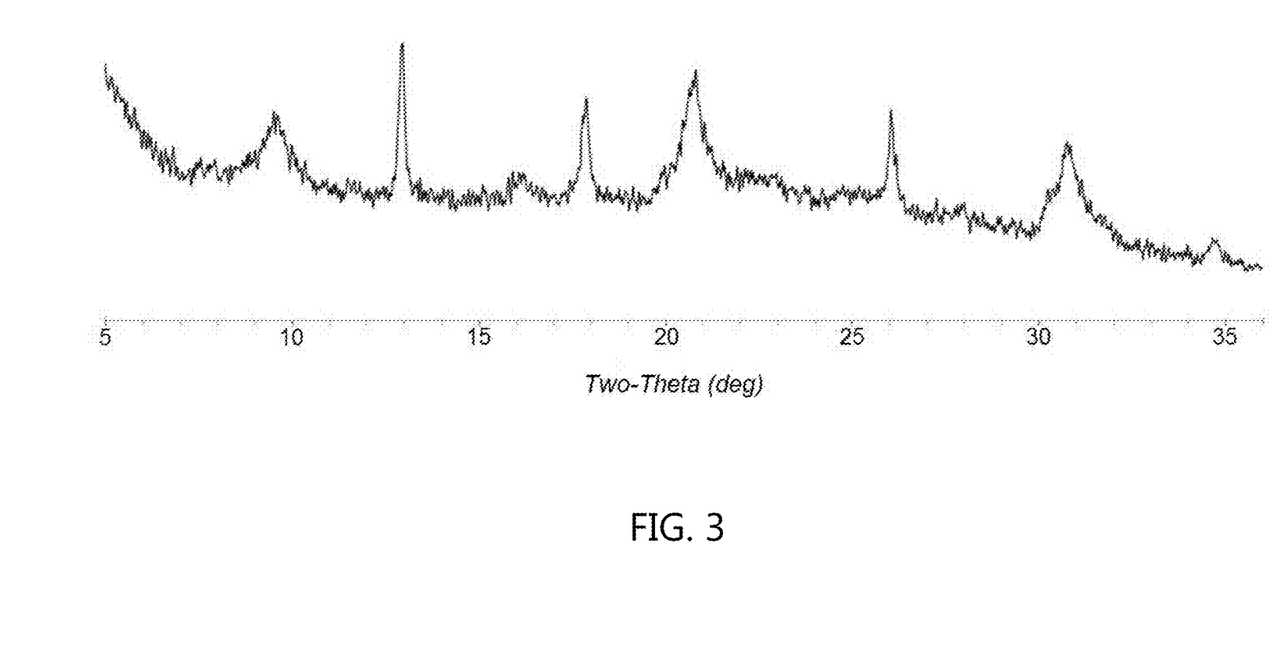
FIG. 3 shows the powder XRD pattern of the calcined molecular sieve of Example 7.

Powder XRD of the calcined product gave the pattern indicated in FIG. 3 and showed the material to be stable after calcination to remove the organic structure directing agent.

Example 8

The calcined molecular sieve material of Example 7 was treated with 10 mL (per g of molecular sieve) of a 1N ammonium nitrate solution at 90° C. for 2 hours. The mixture was cooled, the solvent decanted off and the same process repeated.

After drying, the product (NH$_4$—SSZ-107) was subjected to micropore volume analysis using N$_2$ an adsorbate and via the B.E.T. method. The molecular sieve had a micropore volume of 0.18 cm$^3$/g.

The invention claimed is:

1. A molecular sieve having, in its as-synthesized form, an X-ray diffraction pattern including the peaks listed in the following Table:

| 2-Theta | d-Spacing, nm | Relative Intensity | Peak Broadening |
|---|---|---|---|
| 7.58 ± 0.20 | 1.166 | W | B |
| 9.59 ± 0.20 | 0.922 | M | B |
| 12.93 ± 0.20 | 0.684 | M | Sh |
| 14.09 ± 0.20 | 0.628 | W | B |
| 16.16 ± 0.20 | 0.548 | W | B |
| 17.78 ± 0.20 | 0.498 | M | Sh |
| 20.03 ± 0.20 | 0.443 | W | B |
| 20.74 ± 0.20 | 0.428 | VS | B |
| 22.04 ± 0.20 | 0.403 | W | Sh |
| 22.51 ± 0.20 | 0.395 | W | Sh |
| 23.26 ± 0.20 | 0.382 | W | B |
| 25.18 ± 0.20 | 0.353 | W | B |
| 26.05 ± 0.20 | 0.342 | M | Sh |
| 27.89 ± 0.20 | 0.320 | W | B |
| 30.30 ± 0.20 | 0.295 | M | B |
| 30.82 ± 0.20 | 0.290 | S | B |
| 31.47 ± 0.20 | 0.284 | W | B. |

2. The molecular sieve of claim 1, and having a composition comprising the molar relationship:

| SiO$_2$/Al$_2$O$_3$ | 5 to 25 |
| Q/SiO$_2$ | >0 to 0.1 |
| M/SiO$_2$ | >0 to 0.1 | wherein Q comprises 1,1-diethylpyrrolidinium cations and M is a Group 1 or Group 2 metal.

3. The molecular sieve of claim 1, and having a composition comprising the molar relationship:

| SiO$_2$/Al$_2$O$_3$ | 5 to 15 |
| Q/SiO$_2$ | >0 to 0.1 |
| M/SiO$_2$ | >0 to 0.1 | wherein Q comprises 1,1-diethylpyrrolidinium cations and M is a Group 1 or Group 2 metal.

4. A method of synthesizing the molecular sieve of claim 1, the method comprising:
  (a) preparing a reaction mixture comprising:
    (1) a source of silicon oxide;
    (2) a source of aluminum oxide;
    (3) a source of a Group 1 or Group 2 metal (M);
    (4) a structure directing agent (Q) comprising 1,1-diethylpyrrolidinium cations;
    (5) hydroxide ions; and
    (6) water; and
  (b) subjecting the reaction mixture to crystallization conditions sufficient to form crystals of the molecular sieve.

5. The method of claim 4, wherein the reaction mixture has a composition, in terms of mole ratios, as follows:

| | |
|---|---|
| SiO$_2$/Al$_2$O$_3$ | 5 to 100 |
| M/SiO$_2$ | 0.05 to 1.00 |
| Q/SiO$_2$ | 0.05 to 0.50 |
| OH/SiO$_2$ | 0.10 to 1.00 |
| H$_2$O/SiO$_2$ | 10 to 100. |

6. The method of claim 4, wherein the reaction mixture has a composition, in terms of mole ratios, as follows:

| | |
|---|---|
| SiO$_2$/Al$_2$O$_3$ | 15 to 80 |
| M/SiO$_2$ | 0.10 to 0.50 |
| Q/SiO$_2$ | 0.10 to 0.35 |
| OH/SiO$_2$ | 0.20 to 0.60 |
| H$_2$O/SiO$_2$ | 10 to 40. |

7. The method of claim 4, wherein the crystallization conditions include a temperature of from 100° C. to 200° C.

8. A molecular sieve having, in its calcined form, an X-ray diffraction pattern including the peaks listed in the following Table:

| 2-Theta | d-Spacing, nm | Relative Intensity | Peak Broadening |
|---|---|---|---|
| 7.54 ± 0.20 | 1.172 | W | B |
| 9.50 ± 0.20 | 0.930 | M | B |
| 12.94 ± 0.20 | 0.684 | S | Sh |
| 14.09 ± 0.20 | 0.628 | W | B |
| 16.16 ± 0.20 | 0.548 | W | B |
| 17.84 ± 0.20 | 0.498 | M | Sh |
| 20.03 ± 0.20 | 0.443 | W | B |
| 20.74 ± 0.20 | 0.428 | VS | B |
| 22.91 ± 0.20 | 0.388 | W | Sh |
| 24.70 ± 0.20 | 0.360 | W | B |
| 26.03 ± 0.20 | 0.342 | M | Sh |
| 27.98 ± 0.20 | 0.319 | W | B |
| 30.34 ± 0.20 | 0.294 | M | B |
| 30.74 ± 0.20 | 0.291 | S | B |
| 31.78 ± 0.20 | 0.281 | W | B. |

9. The molecular sieve of claim 8, and having a composition comprising the molar relationship:

Al$_2$O$_3$:(*n*)SiO$_2$ wherein n has a value of from 5 to 25.

10. An organic compound conversion process comprising contacting an organic compound under organic compound conversion conditions with a catalyst comprising the molecular sieve of claim 8.

11. The organic compound conversion process of claim 10, wherein the organic compound comprises an organic oxygenate compound and the organic compound conversion process converts the organic oxygenate compound to a product comprising olefins.

12. The organic compound conversion process of claim 11, wherein the organic oxygenate compound comprises methanol, dimethyl ether, or a combination thereof and the olefins comprise ethylene, propylene, or a combination thereof.

13. A process of selectively reducing nitrogen oxides (NO$_x$), comprising contacting a gaseous stream containing nitrogen oxides with a catalyst comprising the molecular sieve of claim 8.

14. The process of claim 13, wherein the catalyst further comprises a transition metal selected from or more of Cr, Mn, Fe, Co, Ce, Ni, Cu, Mo, Ru, Rh, Pd, Ag, Re, Ir, and Pt.

15. The process of claim 14, wherein the transition metal is present in an amount of 0.1 to 10 wt. %, based on the total weight of the molecular sieve.

* * * * *